(12) United States Patent
Dorn et al.

(10) Patent No.: US 6,429,206 B2
(45) Date of Patent: Aug. 6, 2002

(54) NON-SYSTEMIC CONTROL OF PARASITES

(75) Inventors: Hubert Dorn, Wuppertal (DE); Terence Hopkins, Tamborine (AU)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/781,108

(22) Filed: Feb. 9, 2001

Related U.S. Application Data

(62) Division of application No. 08/925,372, filed on Sep. 8, 1997, now Pat. No. 6,232,328, which is a continuation of application No. 08/440,428, filed on May 12, 1995, now abandoned.

(30) Foreign Application Priority Data

May 20, 1994 (DE) .......................... 44 17 742

(51) Int. Cl.⁷ ...................... A61K 31/54; A61K 31/535; A01N 43/40
(52) U.S. Cl. ................ 514/226.8; 514/227.2; 514/227.5; 514/227.8; 514/228.8; 514/235.5; 514/236.6; 514/236.8; 514/318; 514/326
(58) Field of Search ............ 514/226.8, 227.8, 514/228.8, 235.5, 236.8, 318, 326, 227.2, 227.5, 236.6

(56) References Cited

U.S. PATENT DOCUMENTS

| | | | |
|---|---|---|---|
| 4,742,060 A | 5/1988 | Shiokawa et al. | 514/252 |
| 4,874,753 A | 10/1989 | Baker | 514/89 |
| 4,914,113 A | 4/1990 | Shiokawa et al. | 514/333 |
| 5,063,236 A | 11/1991 | Gsell | 514/318 |
| 5,302,605 A | 4/1994 | Kristiansen et al. | 514/341 |

FOREIGN PATENT DOCUMENTS

| | | |
|---|---|---|
| CH | 114 863 | 3/1926 |
| DE | 587 853 | 10/1933 |
| EP | 192060 | 8/1986 |
| EP | 0 268 915 | 6/1988 |
| EP | 285985 | 10/1988 |
| EP | 302389 | 2/1989 |
| EP | 306696 | 3/1989 |
| EP | 315826 | 5/1989 |
| EP | 364844 | 4/1990 |
| EP | 375907 | 7/1990 |
| EP | 376279 | 7/1990 |
| EP | 381130 | 8/1990 |
| EP | 383091 | 8/1990 |
| EP | 386565 | 9/1990 |
| EP | 0 413610 | 2/1991 |
| EP | 042 89 41 | 5/1991 |
| EP | 471372 | 2/1992 |
| EP | 0 483052 | 4/1992 |
| EP | 493369 | 7/1992 |
| EP | 529680 | 3/1993 |
| GB | 2228003 | 8/1990 |
| GB | 2271110 | 4/1994 |
| WO | 91/17 659 | 11/1991 |
| WO | 93/24002 | 12/1993 |

OTHER PUBLICATIONS

Mehlhorn et al., Parasitol Res., 85: 625–637 (1999).
A. Elbert, et al., Pflanzenschutz–Nachrichten Bayer, vol. 44, No. 2, pp. 113–136, (1991).
Derwent Abstract of JP 02–207,076, p. 3, (Aug. 16, 1990).
Derwent Abstract of JP 03,279,359, p. 9, (Dec. 10, 1991).
Derwent Abstract of JP 03–255,072, p.4, (Nov. 13, 1991).
Chemical Abstracts, vol. 91, Abstract No. 69959r, p. 188, (1979).
Derwent Abstract of JP 03–246,283, p. 5, (Nov. 1, 1991).
Derwent Abstract of JP 03–220,176, p. 6, (Sep. 27, 1991).
S.W. Jones, P. Sudershan, R.D. O'Brien, Section of Neurobiology and Behavior, Cornell University Ithaca, NY Interaction of Insecticides with Acetylcholine Receptors.
Derwent Database, AN 66–10652F.
S.W. Jones, et al., Chemical Abstracts, vol. 91, p. 1323Y, (1979).
A. Elbert, et al., Brighton Crop. Protection Conference, pp. 21–28, (1990).

*Primary Examiner*—Allen J. Robinson
(74) *Attorney, Agent, or Firm*—Norris McLaughlin & Marcus

(57) ABSTRACT

Use of agonists and antagonists of the nicotinergic acetylcholine receptors of insects for the non-systemic control of parasitic insects, such as fleas, lice and flies, on humans and on animals.

5 Claims, No Drawings

NON-SYSTEMIC CONTROL OF PARASITES

This application is a division of U.S. Ser. No. 08/925,372, filed on Sep. 8, 1997, now U.S. Pat. No. 6,232,328, which is a continuation of U.S. Ser. No. 08/440,428, filed May 12, 1995, now abandoned.

The present invention relates to the non-systemic control of parasitic insects on humans and animals by means of agonists or antagonists of the nicotinergic acetylcholine receptors in insects.

Agonists or antagonists of the nicotinergic acetylcholine receptors of insects are known. They include the nicotinyl insecticides, very particularly the chloronicotinyl insecticides. It is also known that these compounds have an outstanding action against plant-injurious insects. The systemic action of these compounds in plants against plant-injurious insects is also known.

PCT Application WO 93/24 002 discloses that certain 1-[N-(halo-3-pyridylmethyl)-N-methylamino-1-alkylamino-2-nitroethylene derivatives are suitable for the systemic use against fleas on domestic animals. In this type of application, the active compound is administered orally or parenterally to the domestic animal, for example by means of an injection, thus entering the blood stream of the domestic animal. The fleas then take up the active compound when they suck blood. WO 93/24 002 alleges that the non-systemic type of use is unsuitable for controlling fleas on domestic animals.

Surprisingly, it has now been found that these very agonists or antagonists of the nicotinergic acetylcholine receptors in insects are particularly suitable for the non-systemic control of parasitic insects such as fleas, lice or flies on humans and animals.

Foreign Countries disclosed, for example in European Offenlegungsschriften No. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften No. 3 639 877, 3 712 307; Japanese Offenlegungsschriften No. 03 220 176, 02 207 083, 63 307 857, 63 287 764, 03 246 283, 04 9371, 03 279 359, 03 255 072; U.S. Pat. Nos. 5,034,524, 4,948,798, 4,918,086, 5,039,686, 5,034,404; PCT Applications No. WO 91/17 659, 91/4965; French Application No. 2 611 114; Brazilian Application No. 88 03 621.

Reference is made expressly to the methods, processes, formulae and definitions described in these publications and to the individual preparations and compounds described therein.

These compounds may preferably be represented by the general formula (I)

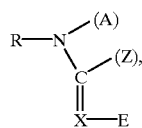

(I)

in which
R represents hydrogen, optionally substituted radicals from the group consisting of acyl, alkyl, aryl, aralkyl, heteroaryl or heteroatyalkyl;
A represents a monofunctional group from the series consisting of hydrogen, acyl, alkyl and aryl, or represents a bifunctional group which is linked to the radical Z;
E represents an electron-attracting radical;
X represents the radicals —CH= or =N—, it being possible for the radical —CH= to be linked to the radical Z instead of an H atom;
Z represents a monofunctional group from the series consisting of alkyl, —O—R, —S—R and

or represents a bifunctional group which is linked to the radical A or the radical X.

Particularly preferred compounds of the formula (I) are those in which the radicals have the following meanings:
R represents hydrogen and optionally substituted radicals from the series consisting of acyl, alkyl, aryl, aralkyl, heteroaryl and heteroarylalkyl.

Acyl radicals which may be mentioned are formyl, alkylcarbonyl, arylcarbonyl, alkylsulphonyl, arylsulphonyl or (alkyl)-(aryl)-phosphoryl all of which may, in turn, be substituted.

Alkyl which may be mentioned is $C_{1-10}$-alkyl, in particular $C_{1-4}$-alkyl, specifically methyl, ethyl, i-propyl and sec- or t-butyl, all of which can, in turn, be substituted.

Aryl which may be mentioned is phenyl or naphthyl, in particular phenyl.

Aralkyl which may be mentioned is phenylmethyl or phenethyl.

Heteroaryl which may be mentioned is heteroaryl having up to 10 ring atoms and N, O, S, in particular N, as hetero atoms. The following may be mentioned specifically: thienyl, furyl, thiazolyl, imidazolyl, pyridyl and benzothiazolyl.

Heteroarylalkyl which may be mentioned is heteroarylmethyl or heteroarylethyl having up to 6 ring atoms and N, O, S, in particular N, as heteroatoms.

The following substituents may be mentioned by way of example and as being preferred:
alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different, and preferred halogen atoms being fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methyl-ethyl-amino, n- and i-propylamino and methyl-n-butylamino; carboxyl; carbalkoxy having preferably 2 to 4, in particular 2 or 3, carbon atoms such as carbomethoxy and carboethoxy; sulpho (—$SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino, such as chloropyridylamino and chloropyridylmethylamino.

A particularly preferably represents hydrogen and also optionally substituted radicals from the series consisting of acyl, alkyl and aryl, all of which preferably have the meanings given in the case of R. A furthermore represents a bifunctional group. The following group may be mentioned: optionally substituted alkylene having 1–4, in particular 1–2, C atoms, suitable substituents which may be mentioned being those listed further above and it being possible for the alkylene groups to be interrupted by hetero atoms from the series consisting of N, O and S.

A and Z together with the atoms to which they are bonded can form a saturated or unsaturated heterocyclic ring. The heterocyclic ring can contain a further 1 or 2 identical or different hetero atoms and/or hetero groups. Hetero atoms are preferably oxygen, sulphur or nitrogen, and hetero groups are N-alkyl, the alkyl of the N-alkyl group preferably containing 1 to 4, in particular 1 or 2, carbon atoms. Alkyl which may be mentioned is methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, hexahydro-1,3,5-triazine and morpholine, all of which can optionally be substituted, preferably by methyl.

E represents an electron-attracting radical, radicals which may be mentioned being, in particular, $NO_2$, CN and halogenoalkylcarbonyl such as 1,5-halogeno-$C_{1-4}$-carbonyl, in particular $COCF_3$.

X represents —CH= or —N=.

Z represents optionally substituted radicals alkyl, —OR, —SR and —NRR, R and the substituents preferably having the abovementioned meaning.

Z can not only form the abovementioned ring, but can also, together with the atom to which it is bonded and the radical

instead of X, form a saturated or unsaturated heterocyclic ring. The heterocyclic ring can contain a further 1 or 2 identical or different hetero atoms and/or hetero groups. Hetero atoms are preferably oxygen, sulphur or nitrogen, and hetero groups are N-alkyl, the alkyl or N-alkyl group preferably containing 1 to 4, in particular 1 or 2, carbon atoms. Alkyl which may be mentioned is methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazine.

The compounds of the general formulae (II) and (III) may be mentioned as compounds which can be used very particularly preferably according to the invention:

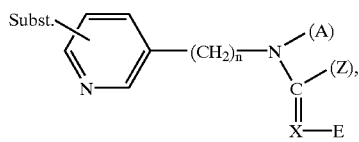
(II)

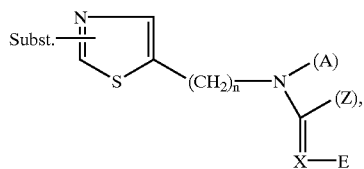
(III)

in which n represents 1 or 2,

Subst. represents one of the abovementioned substituents, in particular halogen, very particularly chlorine, and A, Z, X and E have the abovementioned meanings.

The following compounds may be mentioned specifically:

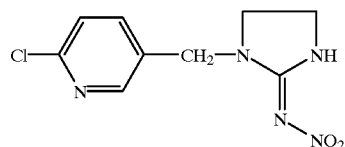

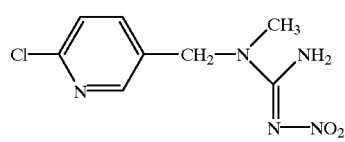

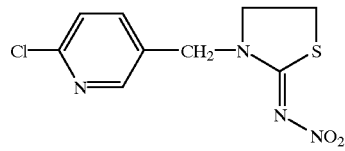

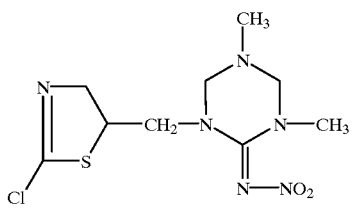

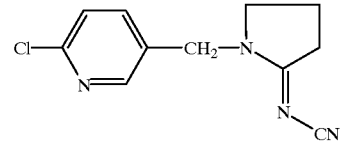

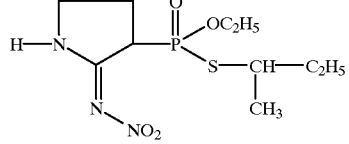

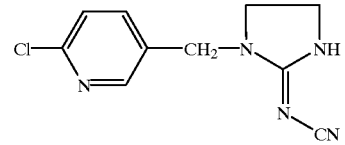

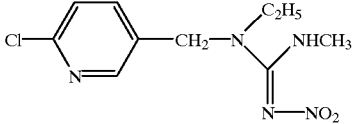

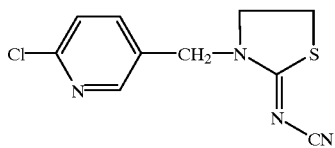
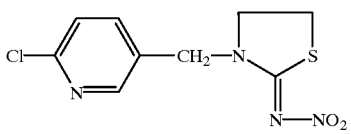
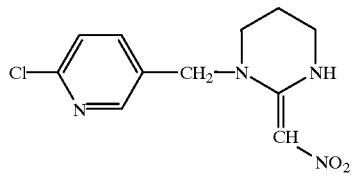
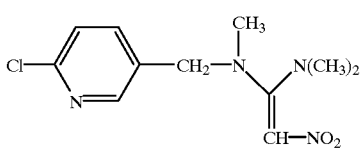
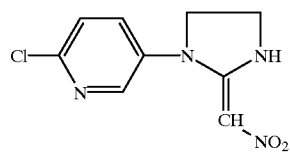
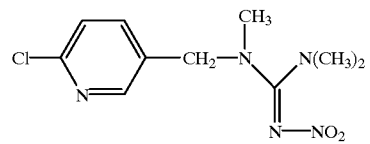
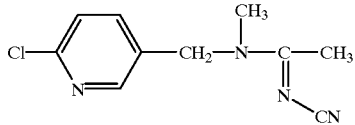
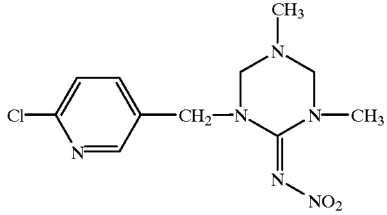
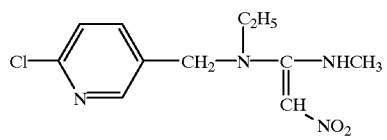
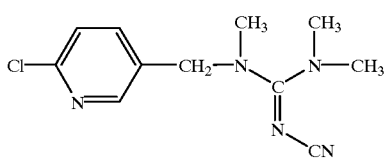

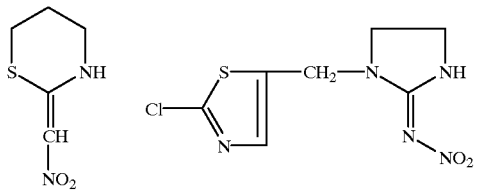
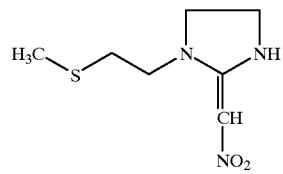
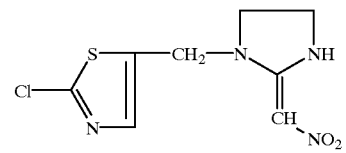

The active compounds are suitable for the control of parasitic insects which can be found in humans and in animal keeping and livestock breeding in domestic animals, productive livestock, zoo animals, laboratory animals, experimental animals and pets, while having favourable toxicity to warm-blooded species. They are active against all or individual development stages of the pests and against resistant and normally sensitive pest species.

The pests include:

From the order of the Anoplura, for example, Haematopinus spp., Linognathus spp., Solenopotes spp., Pediculus spp., Pthirus spp;

From the order of the Mallophaga, for example, Trimenopon spp., Menopon spp., Eomenacanthus spp., Menacanthus spp., Trichodectes spp., Felicola spp., Damalinea spp., Bovicola spp;

From the order of the Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cordylobia spp., Cochliomyia spp., Chrysomyia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp.

From the order of the Siphonaptera, for example, Ctenocephalides spp., Echidnophaga spp., Ceratophyllus spp.

Particular mention may be made of the action against Siphonaptera, in particular against fleas.

Particularly mentioned are the following animals.

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys and ducks.

Laboratory and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, dermally, by environment treatment, or with the aid of active-compound-containing shaped articles such as, for example, strips, plates, bands, collars, ear marks, limb bands, marking devices.

Dermal administration is effected, for example, in the form of bathing, dipping, spraying, pouring on, spotting on, washing, shampooing, pouring over, and dusting.

Suitable preparations are:

solutions or concentrates for administration after dilution, solutions for use on the skin, pour-on and spot-on formulations, gels;

emulsions and suspensions for dermal administration, and semi-solid preparations;

formulations in which the active compound is incorporated into a cream base or into an oil-in-water or water-in-oil emulsion base;

solid preparations such as powders, or shaped articles containing active compound.

Solutions for use on the skin are applied dropwise, brushed on, rubbed in, sprayed on, splashed on, or applied by dipping, bathing or washing.

The solutions are prepared by dissolving the active compound in a suitable solvent and, if appropriate, adding additives such as solubilizers, acids, bases, buffer salts, antioxidants and preservatives.

The following may be mentioned as solvents: physiologically acceptable solvents such as water, alcohols such as ethanol, butanol, benzyl alcohol, glycerol, hydrocarbons, propylene glycol, polyethylene glycols, N-methyl-pyrrolidone, and mixtures of these.

If appropriate, the active compounds can also be dissolved in physiologically acceptable vegetable or synthetic oils.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

It may be advantageous to add thickeners during the preparation of the solutions. Thickeners are: inorganic thickeners such as bentonites, colloidal silica, aluminium monostearate, organic thickeners such as cellulose derivatives, polyvinyl alcohols and their copolymers, acrylates and methacrylates.

Gels, which are applied to, or brushed onto, the skin, are prepared by treating solutions which have been prepared as described above with such an amount of thickener that a clear substance of cream-like consistency is formed. Thickeners applied are the thickeners indicated further above.

Pour-on and spot-on formulations are poured or sprayed onto limited areas of the skin, the active compound spreading on the body surface.

Pour-on and spot-on formulations are prepared by dissolving, suspending or emulsifying the active compound in suitable solvents or solvent mixtures which are tolerated by the skin. If appropriate, other adjuvants such as colorants, antioxidants, light stabilizers and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers, such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone, 2-dimethyl-4-oxy-methylene-1,3-dioxolane.

Colorants are all colorants which are licensed for use on animals and which can be dissolved or suspended.

Adjuvants are also spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Examples of light stabilizers are substances from the benzophenone class, or novantisolic acid.

Examples of tackifiers are cellulose derivatives, starch derivatives, polyacrylates, natural polymers such as alginates, gelatin.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colorants, absorption accelerators, preservatives, antioxidants, light stabilizers, viscosity-increasing substances.

The following may be mentioned as the hydrophobic phase (oils): par oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxy groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, and other fatty alcohols such as isotridecyl alcohol, 2-octyldodecanol, cetylstearyl alcohol and oleyl alcohol.

Fatty acids such as, for example, oleic acid and its mixtures.

The following may be mentioned as the hydrophilic phase:

water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as di-sodium N-lauryl-β-iminodipropionate or lecithin;

anionic surfactants such as Na lauryl sulphate, fatty alcohol ether sulphates, the monoethanolamine salt of mono/dialkyl polyglycol ether orthophosphoric esters;

cationic surfactants such as cetyltrimethylammonium chloride.

The following may be mentioned as other adjuvants: viscosity-increasing substances and substances which stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions are prepared by suspending the active compound in an excipient liquid, if appropriate with an addition of further adjuvants such as wetting agents, colorants, absorption accelerators, preservatives, antioxidants and light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations for dermal administration are only distinguished from the above-described suspensions and emulsions by their higher viscosities.

To prepare solid preparations, the active compound is mixed with suitable carriers, if appropriate with the addition of adjuvants, and the mixture is formulated as desired.

Carriers which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Adjuvants are preservatives, antioxidants and colorants which have already been indicated further above.

Other suitable adjuvants are lubricants and glidants such as, for example, magnesium stearate, stearic acid, talc and bentonites.

Ready-to-use preparations contain the active compound in concentrations from 1 ppm-20 percent by weight, preferably 0.01–10 percent by weight.

Preparations which are diluted prior to use contain the active compound in concentrations of 0.5–19 percent by weight, preferably 1 to 50 percent by weight.

In general, it has proved advantageous to administer amounts of approximately 0.5 to approximately 50 mg, preferably 1 to 20 mg, of active compound per kg of body weight per day, to achieve effective results.

Particular mention may be made of the use via shaped articles. Shaped articles are, inter alia, collars, attachments for collars (medallions), ear tags, bands which are affixed to limbs or parts of the body, adhesive strips and films, and peel-off films.

Particular mention may be made of collars and medallions.

Suitable polymers for the preparation of the shaped articles are thermoplastic and flexible, heat-curable polymers and also elastomers and thermoplastic elastomers. Polymers which may be mentioned are polyvinyl resins, polyurethanes, polyacrylates, epoxy resins, cellulose, cellulose derivatives, polyamides and polyesters which are sufficiently compatible with the abovementioned active compound. The polymers must be sufficiently strong and flexible so as not to tear or become brittle upon shaping. They must be sufficiently stable so as to be resistant to normal wear and tear. Moreover, the polymers must allow sufficient migration of the active compound towards the surface of the shaped article.

Other polyvinyl resins include polyvinyl halides such as polyvinyl chloride, polyvinyl chloride/vinyl acetate and polyvinyl fluoride; polyacrylate and polymethacrylate esters, such as polymethyl acrylate and polymethyl methacrylate; and polyvinylbenzenes, such as polystyrene and polyvinyltoluene. Particular mention may be made of polyvinyl chloride.

Plasticizers which are suitable for the preparation of the polyvinyl-resin-based shaped articles are those which are conventionally used for plasticizing solid vinyl resins. The choice of plasticizer to be used depends on the resin and its compatibility with the plasticizer. Examples of suitable plasticizers are esters of phosphoric acid, such as esters of phthalic acid, such as dimethyl phthalate and dioctyl phthalate, and esters of adipic acid, such as diisobutyl adipate. It is also possible to use other esters, such as the esters of azelaic acid, maleic acid, ricinoleic acid, myristic acid, palmitic acid, oleic acid, sebacic acid, stearic acid and trimellithic acid, as well as complex linear polyesters, polymeric plasticizers and epoxidized soyabean oils. The quantity of the plasticizer amounts to approximately 10 to 50% by weight, preferably approximately 20 to 45% by weight, of the entire composition.

The shaped articles may furthermore comprise other constituents such as stabilizers, lubricants, fillers and colorants, without this altering the basic characteristics of the composition. Suitable stabilizers are antioxidants and agents which protect the bands against ultraviolet radiation and undesirable degradation during working, such as extruding. Moreover, some stabilizers, such as epoxidized soya bean oils, also act as secondary plasticizers. Examples of lubricants which can be used are stearates, stearic acid and low-molecular-weight polyethylenes. These components may be used in a concentration of up to approximately 5% by weight of the entire composition.

When preparing the vinyl-based shaped articles, the various components are mixed by known processes and subjected to compression moulding by known extruding or injection moulding processes.

From the technical point of view, the choice of the processing process for the preparation of the shaped articles depends essentially on the rheological properties of the band material and the shape of the band desired. The processing processes can be adjusted to suit the processing technology or the type of shaping. In the processing technology, the processes may be classified according to the rheological states which pass through them. Accordingly, suitable processes for viscose materials for bands are casting, compressing, injection moulding and applying, and suitable processes for elastoviscose polymers are injection moulding, extruding (extrusion moulding), calendering, rolling and, if appropriate, edging. Classified by the type of shaping, the shaped articles according to the invention may be prepared by casting, immersing, compressing, injection moulding, extruding, calendering, stamping, bending, thermoforming and the like.

These processing processes are known and need no further explanation. In principle, the illustrations given above by way of example for polyvinyl resins also apply to other polymers.

The polyurethanes acting as carrier material are prepared in a manner known per se by reacting polyisocyanates having high-molecular-weight compounds with at least two groups capable of reacting with isocyanates, and, if appropriate, low-molecular-weight chain extenders and/or monofunctional chain terminators.

Suitable starting components for the preparation of the polyurethanes are aliphatic, cycloaliphatic, araliphatic, aromatic and heterocyclic polyisocyanates, as they are described, for example, by W. Siefken in Liebig's Annalen der Chemie, 562, pages 75 to 136. The following may be mentioned by way of example: ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3-diisocyanate and cyclohexane 1,4-diisocyanate and any desired mixtures of these compounds, 1-isocyanato-3,3,5-trimethyl-5-isocyanatomethyl-cyclohexane (see DE-AS (German Published Specification) 202 785 and U.S. Pat. No. 3,401,190), 2,4- and 2,6-hexahydrotoluylene diisocyanate and any desired mixtures of these compounds; hexahydro-1,3- and/or -1,4-phenylene diisocyanate, perhydro-2,4'- and/or -4,4'-diphenylmethane diisocyanate, 1,3- and 1,4-phenylene diisocyanate, 2,4- and 2,6-toluylene diisocyanate and any desired mixtures of these compounds; diphenylmethane 2,4'-diisocyanate and/or diphenylmethane 4,4'-diisocyanate, naphthylene 1,5-diisocyanate, triphenylmethane 4,4', 4"-triisocyanate, polyphenyl-polymethylene polyisocyanates as they are obtained by aniline/formaldehyde condensation followed by phosgenation and described, for example, in GB Patent Specifications 874 430 and 848 671; m- and p-isocyanatophenol-sulphonyl isocyanates in accordance with U.S. Pat. No. 3,454,606; perchlorinated aryl polyisocyanates as they are described, for example, in DE-AS (German Published Specification) 1 157 601 and in U.S. Pat. No. 3,277,138; polyisocyanates having carbodiimide groups, as they are described in German Patent Specification 1 092 007 and in U.S. Pat. No. 3,152,162; diisocyanates as they are described in U.S. Pat. No. 3,492,330; polyisocyanates having allophanate groups as they are described, for example, in British Patent Specification 994 890, German Patent Specification 761 626 and the published Dutch Patent Application 7 102 524; polyisocyanates having isocyanurate groups, as they are described, for example, in U.S. Pat. No. 3,001,973, in German Patent Specifications 1 022 789, 1 222 067 and 1 027 394 and in DE-OS (German Published Specifications) 1 929 034 and 2 004 048; polyisocyanates having urethane groups, as they are described, for example, in German Patent Specification 752 261 or in U.S. Pat. No. 3,394,164; polyisocyanates having acylated urea groups, in accordance with German Patent Specification 1 230 778; polyisocyanates having biuret groups, as they are described, for example, in German Patent Specification 1 101 394, in U.S. Pat. Nos. 3,124,605 and 3,201,372, and in British Patent Specification 889 050; polyisocyanates prepared by telomerization reactions, as they are described, for example, in U.S. Pat. No. 3,654,106; polyisocyanates having ester groups, as they are mentioned in, for example, British Patent Specifications 965 474 and 1 072 956, in U.S. Pat. No. 3,567,763 and in German Patent Specification 1 231 688; reaction products of the abovementioned isocyanates with acetals in accordance with German Patent Specification 1 072 385, and polyisocyanates containing polymeric fatty acid radicals, in accordance with U.S. Pat. No. 3,455,883.

It is also possible to employ the distillation residues which have isocyanate groups and which are obtained in the preparation of isocyanate on a technical scale, if appropriate dissolved in one or more of the abovementioned polyisocyanates. It is furthermore possible to employ any desired mixtures of the abovementioned polyisocyanates.

Preferred polyisocyanates are, in general, the toluylene diisocyanates and the diphenylmethane diisocyanates.

Starting components for the preparation of the polyurethanes are furthermore compounds of a molecular weight of, as a rule, 400–10,000 which have at least two hydrogen atoms which are reactive towards isocyanates. Besides compounds which have amino groups, thiol groups or carboxyl groups, these are preferably to be understood as meaning polyhydroxyl compounds, in particular compounds having two to eight hydroxyl groups, specifically those of a molecular weight of 800 to 10,000, preferably 1,000 to 6,000, for example polyesters, polyethers, polythioethers, polyacetals, polycarbonates and polyester amides having at least two, as a rule 2–8, but preferably 2–4, hydroxyl groups, as they are known per se for the preparation of homogeneous and cellular polyurethanes.

Examples of suitable polyesters having hydroxyl groups are reaction products of polybasic, preferably dibasic and, if appropriate, additionally tribasic, carboxylic acids. Instead of the free polycarboxylic acids, it is also possible to use the corresponding polycarboxylic anhydrides or the corresponding polycarboxylates of lower alcohols or their mixtures for preparing the polyesters. The polycarboxylic acids can be of aliphatic, cycloaliphatic, aromatic and/or heterocyclic nature and can optionally be substituted, for example by halogen atoms, and/or unsaturated.

Examples which may be mentioned are: succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids such as oleic acid, if appropriate as a mixture with monomeric fatty acids, dimethyl terephthalate and terephthalic acid bis-glycol ester.

Examples of suitable polyhydric alcohols are ethylene glycol, propylene-1,2- and -1,3-glycol, butylene-1,4- and -2,3-glycol, hexane-1,6-diol, octane-1,8-diol, neopentyl glycol, cyclohexanedimethanol(1,4-bis-hydroxymethylcyclohexane), 2-methyl-1,3-propanediol, glycerol, trimethylolpropane, hexane-1,2,6-triol, butane-1,2,4-triol, trimethylethane, pentaerythritol, quinitol, mannitol and sorbitol, methylglycositol, furthermore diethylene glycol, triethylene glycol, tetraethylene glycol, polyethylene glycols, dipropylene glycol, polypropylene glycols, dibutylene glycol and polybutylene glycols. The polyesters may proportionately have terminal carboxyl groups. Polyesters of lactones, for example $\epsilon$-caprolactone, or hydroxycarboxylic acids, for example $\omega$-hydroxycaproic acid, may also be employed.

Suitable polyhydric alcohols are polyethers which have at least two, as a rule two to eight, preferably two to three, hydroxyl groups. These are known per se and are prepared, for example, by polymerizing epoxides, such as ethylene oxide, propylene oxide, butylene oxide, tetrahydrofan, styrene oxide or epichlorohydrin, with themselves, for example in the presence of $BF_3$, or by an addition reaction of these epoxides, if appropriate as a mixture or in succession, with starting components having reactive hydrogen atoms, such as water, alcohols, ammonia or amines, for example ethylene glycol, propylene-1,3-glycol or propylene-1,2-glycol, trimethylolpropane, 4,4'-dihydroxy diphenylpropane, aniline, ethanolamine or ethylenediamine. Other suitable substances are sucrose polyethers as they are described, for example, in DE-AS (German Published Specifications) 1 176 358 and 1 064 938. Frequently, those polyethers which have predominantly (up to 90% by weight based on all OH groups present in the polyether) primary OH groups are preferred. Other suitable substances are polyethers which are modified by vinyl polymers, as they are formed, for example, by polymerizing styrene and acrylonitrile in the presence of polyethers (U.S. Pat. Nos. 3,383,351, 3,304,273, 3,523,093, 3,110,695, German Patent Specification 1 152 36), as are polybutadienes having OH groups.

Amongst the polythioethers, particular mention may be made of the condensation products of thiodiglycol with itself and/or with other glycols, dicarboxylic acids, formaldehyde, aminocarboxylic acids or amino alcohols. Depending on the co-components, the products are mixed polythioethers, or polythioetherates or polythioetheramidates.

Suitable polyacetals are, for example, those compounds which can be prepared from glycols, such as diethylene glycol, triethylene glycol, 4,4'-dioxethoxydiphenyl-dimethylmethane, hexanediol and formaldehyde. Polyacetals which are suitable according to the invention may also be prepared by polymerizing cyclic acetals.

Suitable polycarbonates having hydroxyl groups are those of the type known per se, which can be prepared, for example, by reacting diols, such as propane-1,3-diol, butane-1,4diol and/or hexane-1,6diol, diethylene glycol, triethylene glycol or tetraethylene glycol, with diaryl carbonates, for example diphenyl carbonate, or phosgene.

The polyamidates and polyamides include, for example, the predominantly linear condensates obtained from polybasic saturated and unsaturated carboxylic acids or their anhydrides and polyhydric saturated and unsaturated amino alcohols, diamines, polyamines and their mixtures.

Other substances which can be used are polyhydroxyl compounds which already have urethane or urea groups, as well as optionally modified natural polyols, such as castor oil, or carbohydrates or starch. Other substances which can be employed according to the invention are addition products of alkylene oxides with phenol/formaldehyde resins or else with urea/formaldehyde resins.

Representatives of these compounds are described, for example, in High Polymers, Vol. XVI, "Polyurethans, Chemistry and Technology", by Saunders-Frisch, Interscience Publishers, New York, London, Volume I, 1962, pages 32–42 and pages 44–54 and Volume II, 1964, pages 5–6 and 198–199, and in Kunststoff Handbuch [Plastics Manual], Volume VII, Vieweg Höchtlen, Carl-Hanser-Verlag, Munich, 1966, for example on pages 45–71.

Naturally, it is possible to employ mixtures of the abovementioned compounds of a molecular weight of 400–10,000 which have at least two hydrogen atoms which are reactive towards isocyanates, for example in the form of polyether mixtures.

Other suitable starting components to be employed, if appropriate, are compounds of a molecular weight of 32–400 which have at least two hydrogen atoms which are reactive towards isocyanates. In this case too, such compounds are understood as meaning compounds having hydroxyl groups and/or amino groups and/or thiol groups and/or carboxyl groups, preferably compounds which act as chain extenders or crosslinking agents.

These compounds have, as a rule 2 to 8 hydrogen which are reactive towards isocyanates, preferably 2 or 3 reactive hydrogen atoms.

Examples of such compounds which may be mentioned are:
ethylene glycol, propylene-1,2- and -1,3-glycol, butylene-1,4- and -2,3-glycol, pentane-1,5-diol, hexane-1,6-diol, octane-1,8-diol, neopentyl glycol, 1,4-bis-hydroxymethyl-cyclohexane, 2-methyl-1,3-propanediol, glycerol, trimethylolpropane, hexane-1,2,6-triol, trimethylolethane, pentaerythritol, quinitol, mannitol and sorbitol, diethylene glycol, triethylene glycol, tetraethylene glycol, polyethylene glycols having a molecular weight of up to 400, dipropylene glycol, polypropylene glycols having a molecular weight of up to 400, dibutyllene glycol, polybutylene glycols having a molecular weight of up to 400, 4,4'-dihydroxy-diphenylpropane, di-hydroxymethylhydroquinone, ethanolamine, diethanolamine, triethanolamine, 3-aminopropanol, ethylenediamine, 1,3-diaminopropane, 1-mercapto-3-aminopropane, 4-hydroxy- or -amino-phthalic acid, succinic acid, adipic acid, hydrazine, N,N'-dimethylhydrazine, 4,4'-diaminodiphenylmethane, toluylenediamine, methylene-bis-chloroaniline, methylene-bis-anthranilates, diaminobenzoates and the isomeric chlorophenylene-diamines.

In this case too, mixtures of various compounds of a molecular weight of 32–400 having at least two hydrogen atoms which are reactive towards isocyanates may be used.

However, it is also possible to employ polyhydroxyl compounds which contain high-molecular-weight polyadducts or polycondensates in finely disperse or dissolved form. Such modified polyhydroxyl compounds are obtained when polyaddition reactions (for example reactions between polyisocyanates and amino-functional compounds) or polycondensation reactions (for example between formaldehyde and phenols and/or amines) are allowed to proceed directly in situ in the abovementioned compounds having hydroxyl groups. Such processes are described, for example, in DE-AS (German Published Specifications) 1 168 075 and 1 260 142 and in DE-OS (German Published Specifications) 2 324 134, 2 423 984, 2 512 385, 2 513 815, 2 550 797, 2 550 833 and 2 550 862. However, it is also possible, in accordance with U.S. Pat. No. 3,869,413 or DE-OS (German Published Specification) 2 550 860 to mix a finished aqueous polymer dispersion with a polyhydroxyl compound and subsequently to remove the water from the mixture.

When selecting the higher-molecular-weight polyol component used for the preparation of the polyurethane, it must be borne in mind that the finished polyurethane should not be capable of swelling in water. Thus, using an excess of polyhydroxyl compounds having ethylene oxide units (polyethylene glycol polyethers or polyesters having diethylene glycol or triethylene glycol as diol component) is therefore to be avoided.

Substances which may be particularly emphasized for the preparation of the shaped articles are thermoplastic elastomers. These are materials which comprise elastomeric phases either mixed physically or bonded chemically in polymers which can be processed as thermoplastics. A distinction is made between polyblends, in which the elastomeric phases are a component of the polymeric matrix Hard and soft regions are present side by side as a result of the build-up of the thermoplastic elastomers. The hard regions form a crystalline network structure or a continuous phase, the interstices of which are filled by elastomeric segments. Due to this build-up, these materials have rubber-like properties.

A distinction is made between 5 main groups of thermoplastic elastomers:
1. Copolyesters
2. Polyether block amides (PEBA)
3. Thermoplastic polyurethanes (TPU)
4. Thermoplastic polyolefins (TPO)
5. Styrene block copolymers Suitable copolymers (segmented polyester elastomers) are built up, for example, from a large number of recurring, short-chain ester units and long-chain ester units, which are combined by ester bonds, the short-chain ester units making up about 15–65% by weight of the copolyester and having the formula I.

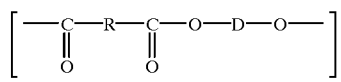

Formula I in which
R represents a divalent radical of a dicarboxylic acid having a molecular weight of less than about 350, and
D represents a divalent radical of an organic diol having a molecular weight of less than about 250.

The long-chain ester units make up about 35–85% by weight of the copolyester and have the formula II

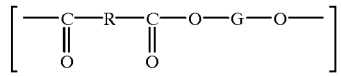

Formula II in which
R represents a divalent radical of a dicarboxylic acid having a molecular weight of less than about 350, and
G represents a divalent radical of a long-chain glycol having an average molecular weight of about 350 to 6000.

The copolyesters which can be used according to the invention can be prepared by polymerizing with one another a) one or more dicarboxylic acids, b) one or more linear, long-chain glycols and c) one or more low-molecular-weight diols.

The dicarboxylic acids for the preparation of the copolyester can be aromatic, aliphatic or cycloaliphatic. The preferred dicarboxylic acids are the aromatic acids having 8–16 C atoms, in particular phenylenedicarboxylic acids, such as phthalic, terephtalic and isophthalic acid.

The low-molecular-weight diols for the reaction to form the short-chain ester units of the copolyesters belong to the classes of acyclic, alicyclic and aromatic dihydroxy compounds. The preferred diols have 2–15 C atoms, such as ethylene glycol, propylene glycol, tetramethylene glycol, isobutylene glycol, pentamethylene glycol, 2,2-dimethyltrimethylene glycol, hexamethylene glycol and decamethylene glycol, dihydroxycyclohexane, cyclohexanedimethanol, resorcinol, hydroquinone and the like. The bisphenols for the present purpose include bis-(p-hydroxy)-diphenyl, bis-(p-hydroxyphenyl)-methane, bis-(p-hydroxyphenyl)-ethane and bis-(p-hydroxyphenyl)-propane.

The long-chain glycols for the preparation of the soft segments of the copolyesters preferably have molecular weights of about 600 to 3000. They include poly(alkyleneether) glycols in which the alkylene groups have 2–9 carbon atoms.

Glycol esters of poly-(alkyleneoxide)-dicarboxylic acids can also be used as the long-chain glycol.

Polyester glycols can also be used as the long-chain glycol.

The long-chain glycols also include polyformals, which are obtained by reaction of formaldehyde with glycols. Polythioether glycols are also suitable. Polybutadiene glycols and polyisoprene glycols, copolymers thereof and saturated hydrogenation products of these materials are satisfactory long-chain polymeric glycols.

Processes for the synthesis of such copolyesters are disclosed in DOS [German Published Specification] 2 239 271, DOS (German Published Specification) 2 213 128, DOS (German Published Specification) 2 449 343 and U.S. Pat. No. 3,023,192.

Suitable copolyesters are obtainable, for example, under the trade names ®Hytrel from Du Pont, ®Pelpren from Toyobo®, Arnitel from Akzo, ®Ectel from Eastman Kodak and ®Riteflex from Hoechst.

Suitable polyether block amides are, for example, those composed of polymer chains which are built up from recurrent units, corresponding to the formula I.

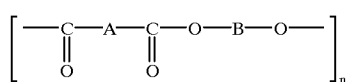

Formula I in which
A is the polyamide chain derived from a polyamide having 2 terminal carboxyl groups by loss of the latter,
B is the polyoxyalkylene glycol chain derived from a polyoxyalkylene glycol having terminal OH groups by loss of the latter, and
n is the number of units forming the polymer chain.

The end groups are preferably OH groups or radicals of compounds which terminate the polymerization.

The dicarboxylic polyamides having terminal carboxyl groups are obtained in a known manner, for example by polycondensation of one or more lactams or/and one or more amino acid, furthermore by polycondensation of a dicarboxylic acid with an amine, in each case in the presence of an excess of an organic dicarboxylic acid, preferably having terminal carboxyl groups. During the polycondensation, these carboxylic acids become a component of the polyamide chain and become attached in particular to the end of this polyamide chain, resulting in an α-ω-dicarboxylic polyamide. The dicarboxylic acid furthermore acts as a chain terminator, which is why it is also employed in an excess.

The polyamide can be obtained starting from lactams and/or amino acids having a hydrocarbon chain composed of 4–14 C atoms, such as, for example, caprolactam, oenantholactar, dodecalactam, undecanolactam, decanolactam, 11-amino-undecano or 12-aminododecanoic acid.

Examples which may be mentioned of polyamides, as they are formed by polycondensation of a dicarboxylic acid with a diamine, are the condensation products of hexamethylenediamine with adipic acid, azelaic acid, sebacic acid and 1,12-dodecanedioic acid, and the condensation products of nonamethylenediamine and adipic acid.

Suitable as dicarboxylic acid used for the synthesis of the polyamide, that is to say, on the one hand, for fixing in each case one carboxyl group at each end of the polyamide chain and, on the other hand, as chain terminator, are those having 4–20 C atoms, in particular alkanedioic acids, such as succinic acid, adipic acid, suberic acid, azelaic acid, sebacic acid, undecanedioic or dodecanedioic acid, furthermore cycloaliphatic or aromatic dicarboxylic acid, such as terephthalic acid, isphthalic acid or cyclohexane-1,4-dicarboxylic acid.

The polyoxyalkylene glycols having terminal OH groups are unbranched or branched and have an alkylene radical having at least 2 C atoms. They are, in particular, polyoxyethylene glycol, polyoxypropylene glycol and polyoxytetramethylene glycol, and their copolymers.

The average molecular weight of these polyoxyalkylene glycols which are terminated by OH groups may vary within a wide range, it is advantageously between 100 and 6000, in particular between 200 and 3000.

The amount by weight of the polyoxyalkylene glycol, based on the total weight of polyoxyalkylene glycol and dicarboxylic polyamide used for the preparation of the PEBA polymer, is 5–85%, preferably 10–50%.

Processes for the synthesis of such PEBA polymers are disclosed in French Patent Specification 7 418 913 (Publication No. 2 273 021), DOS (German Published Specification) 2 802 989, DOS (German Published Specification) 2 837 687, (German Published Specification) 2 523 991, EP-S (European Published Specification) 0 095 893, DOS (German Published Specification) 2 712 987 and DOS (German Published Specification) 2 716 004.

Preferably suitable PEBA polymers are those which, in contrast to those described above, have random structure. To prepare these polymers, a mixture of
1. one or more polyamide-forming compounds from the group of the ω-aminocarboxylic acids or lactams having at least 10 carbon atoms,
2. an α-ω-dihydroxy-polyoxyalkylene glycol,
3. at least one organic dicarboxylic acid
   in a ratio by weight of 1:(2+3) between 30:70 and 98:2, where equivalent amounts of hydroxyl and carbonyl groups are present in (2+3), is heated in the presence of 2 to 30 percent by weight of water, based on the polyamide-forming compounds of the group 1, under the inherent pressure which is established at temperatures of between 23° C. and 30° C., and subsequently, after the water has been removed, reacted further under atmospheric pressure or under reduced pressure at 250 to 280° C. with the exclusion of oxygen.

Such PEBA polymers which are preferably suitable are described, for example, in DE-OS (German Published Specification) 2 712 987.

PEBA polymers which are suitable and preferably suitable can be obtained, for example, under the trade names ®PEBAX by Atochem, ®Vestamid by Hüls AG, ®Grilamid by EMS-Chemie and ®Kellaflex by DSM.

The shaped articles comprise active compound concentrations of 1 to 20% by weight, preferably 5 to 20% by weight, particularly preferably around 10% by weight.

In the case of collars, the active compound concentrations are preferably 1 to 15%, in the case of medallions, pendants and ear tags preferably 5 to 20%, in the case of films and adhesive strips preferably 0.1 to 5%.

In the preparations and shaped articles, the active compounds can be present in the form of a mixture with synergists or other active compounds. The active compounds include insecticides, such as phosphoric or phosphonic acid esters, natural or synthetic pyrethroids, carbamates, amidines, juvenile hormones and juvenoid synthetic active compounds.

The phosphoric or phosphoric acid esters include:
0-ethyl-0-(8-quinolyl) phenyl-thiophosphate (quintiofos),
0,0-diethyl 0-(3-chloro-4methyl-7-coumarinyl) thiophosphate (coumaphos),
0,0-diethyl 0-phenylglyoxylonitrile oxime thiophosphate (phoxim),
0,0-diethyl 0-cyanochlorobenzaldoxime thiophosphate (chlorphoxim),
0,0-diethyl 0-(4-bromo-2,5-dichlorophenyl) phosphorothionate (bromophos-ethyl),
0,0,0',0'-tetraethyl-S,S'-methylene di(phosphorodithionate) (ethion),
2,3-p-dioxanedithiol-S,S-bis(0,0-diethyl phosphorodithionate,
2-chloro-1-(2,4-dichlorophenyl)vinyl diethyl phosphate (chlorfenvinphos),
0,0-dimethyl 0-(3-methyl-4methylthiophenyl) thionophosphate (fenthion).

The carbamates include:
2-isopropoxyphenyl methylcarbamate (propoxur),
1-naphthyl N-methylcarbamate (carbaryl).

The synthetic pyrethroids include compounds of the formula I

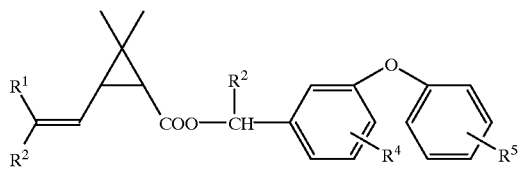

Formula I in which
$R^1$ and $R^2$ represent halogen, optionally halogen-substituted alkyl or optionally halogen-substituted phenyl,
$R^3$ represent hydrogen or CN,
$R^4$ represents hydrogen or halogen and
$R^5$ represents hydrogen or halogen.

Preferred synthetic pyrethroids are those of the formula I in which
$R^1$ represents halogen, in particular fluorine, chlorine or bromine,
$R^2$ represents halogen, in particular, fluorine, chlorine, bromine, trihalogenomethyl, phenyl or chlorophenyl,
$R^3$ represents hydrogen or CN,
$R^4$ represents hydrogen or fluorine and
$R^5$ represents hydrogen.

Particularly preferred synthetic pyrethroids are those of the formula I in which
$R^1$ represents chlorine,
$R^2$ represents chlorine, trifluoromethyl or p-chlorophenyl,
$R^3$ represents CN,
$R^4$ represents hydrogen or fluorine and
$R^5$ represents hydrogen.

Compounds of the formula I which may be mentioned in particular are those in which
$R^1$ represents chlorine,
$R^2$ represents chlorine, or p-chlorophenyl,
$R^3$ represents CN,
$R^4$ represents fluorine in the 4position and
$R^5$ represents hydrogen.

Compounds which may be mentioned specifically are:
(α-cyano-4-fluoro-3-phenoxy)benzyl 3-[2-(4-chlorophenyl)-2-chlorovinyl]-2,2-diethyl-cyclopropanecarboxylate (flumetrin),
α-cyano (4-fluoro-3-phenoxy)-benzyl 2,2-dimethyl-3-(2,2-dichlorovinyl)-cyclopropanecarboxylate (cyfluthrin) and its enantiomers and stereomers,
α-cyano-3-phenoxybenzyl(±)-cis, trans-3-(2,2-dibromovinyl)-2,2-dimethyl-cyclopropanecarboxylate (deltamethrin),
α-cyano-3-phenoxybenzyl 2,2-dimethyl-3-(2,2dichlorovinyl)-cyclopropanecarboxylate (cypermethrin),
3-phenoxybenzyl(±)-cis, trans-3-(2,2-dichlorovinyl)-2,2-dimethyl-cyclopropanecarboxylate (permedrin),
α-cyano-3-phenoxy-benzyl α-(p-Cl-phenyl)-isovalerate (fenvalerate) and
2-cyano-3-phenoxybenzyl 2-(2-chloro-α,α,α-trifluoro-p-toluidino)-3-methylbutyrate (fluvalinate).

The amidines include:
3-methyl-2-[2,4-dimethyl-phenylimino]-tiazoline,
2-(4-chloro-2-methylphenylimino)-3-methylthiazolidine,
2-(4chloro-2-methylphenylimino)3-(isobutyl-1-enyl) thiazolidine and
1,5-bis-(2,4dimethylphenyl)-3-methyl-1,3,5-triazapenta-1,4-diene (amitraz).

The juvenile hormones or juvenile-hormone-like substances include substituted diaryl ethers, benzoylureas and triazine derivatives. The juvenile hormones and juvenile-hormone-like substances include, in particular, compounds of the following formulae:

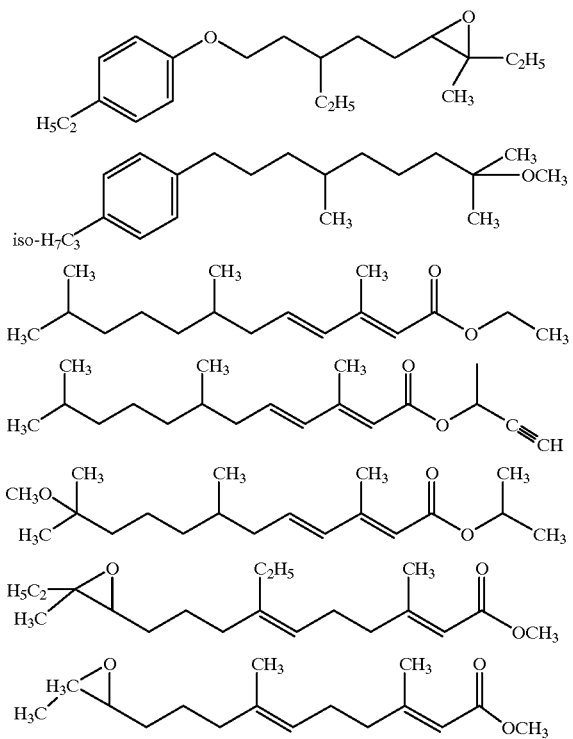

The substituted diaryl ethers include, in particular, substituted alkoxydiphenyl ethers or -diphenylmethanes of the general formula I

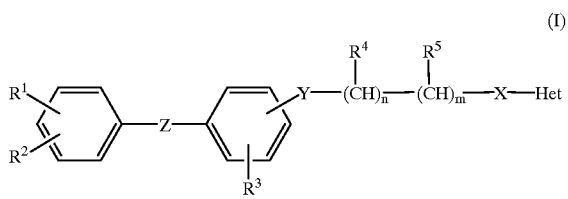

where
$R^1$ represents hydrogen, halogen, alkyl, alkoxy, alkylthio, halogenoalkyl, halogenoalkoxy, halogenoalkylthio, dioxyalkylene, dioxyhalogenoalkylene, CN, $NO_2$, alkenyl, alkinyl, alkoxyalkyl, alkoxyalkoxy or hydroxyalkoxy,
$R^2$ represents the radicals mentioned for $R^1$,
$R^3$ represents the radicals mentioned for $R^1$,
$R^4$ represents hydrogen, alkyl, halogenoalkyl or halogen,
$R^5$ represents the radicals mentioned for $R^4$,
Het represents optionally substituted heteroaryl which is not bonded to the rest of the radical via the heteroatom, X and Y independently of one another represent —O— or —S—,
Z represents —O—, —S—, —$CH_2$—, —$CHCH_3$— or —$C(CH_3)$— and
m and n independently of one another represent 0, 1, 2 or 3, but their sum is equal to or greater than 2.

Particularly preferred compounds of the formula I are those
in which
$R^1$ represents hydrogen, methyl, trifluoromethyl, methoxy, trifluoromethoxy, chlorine or fluorine,
$R^2$ represents hydrogen,
$R^3$ represents hydrogen, fluorine, chlorine or methyl,
$R^4$ represents hydrogen or methyl,
$R^5$ represents methyl, ethyl, trifluoromethyl or hydrogen,
Het represents pyridyl or pyridazinyl which are optionally substituted by fluorine, chlorine, methyl, $NO_2$, methoxy or methylmercapto,
X represents O,
Y represents O,
Z represents O, $CH_2$ or —$CH_3)_2$—,
m represents 1 and
n represents 1.

The following compounds may be mentioned specifically:

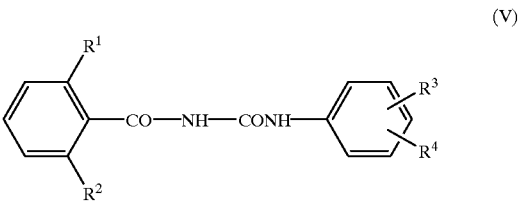

| $R^1$ | $R^3$ | $R^5$ | $R^6$ | Z |
|---|---|---|---|---|
| H | H | $CH_3$ | H | O |
| H | H | $CH_3$ | 2-Cl | O |
| 5-F | H | $CH_3$ | H | O |
| H | H | $CF_3$ | H | O |
| H | H | $C_2H_5$ | H | O |
| H | H | H | H | O |
| H | H | $CH_3$ | H | $CH_2$ |
| H | H | $CH_3$ | H | $C(CH_3)_2$ |

The benzoylureas include compounds of the formula (V):

(V)

[structure: 2,6-disubstituted benzoyl urea with $R^1$, $R^2$ on left ring and $R^3$, $R^4$ on right ring, linked by —CO—NH—CONH—]

where
$R^1$ represents halogen,
$R^2$ represents hydrogen or halogen,
$R^3$ represents hydrogen, halogen or $C_{1-4}$-alkyl and
$R^4$ represents halogen, 1–5-halogeno-$C_{1-4}$-alkyl, $C_{1-4}$-alkoxy, 1–5-halogeno-$C_{1-4}$-alkoxy, $C_{1-4}$-alkylthio, 1–5-halogeno-$C_{1-4}$-alkylthio, phenoxy or pyridyloxy, it being possible for these to be substituted by halogen, $C_{1-4}$-alkyl, 1–5-halogeno-$C_{1-4}$-alkyl, $C_{1-4}$-alkoxy, 1–5-halogeno-$C_{1-4}$-alkoxy, $C_{1-4}$-alkylthio or 1–5-halogeno-$C_{1-4}$-alkylthio.

The following compounds may be mentioned in particular:

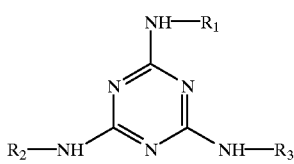

| R¹ | R² | R⁴ |
|---|---|---|
| H | Cl | CF$_3$ |
| Cl | Cl | CF$_3$ |
| F | F | CF$_3$ |
| H | F | CF$_3$ |
| H | Cl | SCF$_3$ |
| F | F | SCF$_3$ |
| H | F | SCF$_3$ |
| H | Cl | OCF$_3$ |
| F | F | OCF$_3$ |
| H | F | OCF$_3$ |
| F | F | O—⟨C$_6$H$_4$⟩—Cl |
| F | F | O—⟨C$_6$H$_4$⟩—CF$_3$ |
| F | F | O—⟨C$_6$H$_4$⟩—CF$_3$ |

The triazines include compounds of the formula (VI)

$$\text{(VI)}$$

triazine with NH—R$_1$, R$_2$—NH, NH—R$_3$ substituents where
R$^1$ represents cyclopropyl or isopropyl;
R$^2$ denotes hydrogen, halogen, C$_1$–C$_{12}$-alkylcarbonyl, cyclopropylcarbonyl, C$_1$–C$_{12}$-alkylcarbamoyl, C$_1$–C$_{12}$-alkyltiocarbamoyl or C$_2$–C$_6$-alkenylcarbamoyl; and
R$^3$ represents hydrogen, C$_1$–C$_{12}$-alkyl, cyclopropyl, C$_2$–C$_6$-alkenyl, C$_1$–C$_{12}$-alkylcarbonyl, cyclopropylcarbonyl, C$_1$–C$_{12}$-alkylcarbamoyl, C$_1$–C$_{12}$-alkylthiocarbamoyl or C$_2$–C$_6$-alkenylcarbamoyl, and their acid addition salts which are non-toxic to warm-blooded species.

Compounds which may be mentioned in particular are:

| R$_1$ | R$_2$ | R$_3$ |
|---|---|---|
| Cyclopropyl | H | H |
| Cyclopropyl | H | CH$_3$ |
| Cyclopropyl | H | C$_2$H$_5$ |
| Cyclopropyl | H | C$_3$H$_7$-n |
| Cyclopropyl | H | C$_4$H$_9$-n |
| Cyclopropyl | H | C$_5$H$_{11}$-n |
| Cyclopropyl | H | C$_6$H$_{13}$-n |
| Cyclopropyl | H | C$_7$H$_{15}$-n |
| Cyclopropyl | H | C$_8$H$_{17}$-n |
| Cyclopropyl | H | C$_{12}$—H$_{25}$-n |
| Cyclopropyl | H | CH$_2$—C$_4$H$_9$-n |
| Cyclopropyl | H | CH$_2$CH(CH$_3$)C$_2$H$_5$ |
| Cyclopropyl | H | CH$_2$CH=CH$_2$ |
| Cyclopropyl | Cl | C$_2$H$_5$ |
| Cyclopropyl | Cl | C$_6$H$_{13}$-n |
| Cyclopropyl | Cl | C$_8$H$_{17}$-n |
| Cyclopropyl | Cl | C$_{12}$H$_{25}$-n |
| Cyclopropyl | H | Cyclopropyl |
| Cyclopropyl | H | COCH$_3$ |
| Cyclopropyl | H | COCH$_3$ HCl |
| Cyclopropyl | H | COC$_2$H$_5$ HCl |
| Cyclopropyl | H | COC$_2$H$_5$ |
| Cyclopropyl | H | COC$_3$H$_7$-n |
| Cyclopropyl | H | COC$_3$H$_7$-i |
| Cyclopropyl | H | COC$_4$H$_9$-t HCl |
| Cyclopropyl | H | COC$_4$H$_9$-n |
| Cyclopropyl | H | COC$_6$H$_{13}$-n |
| Cyclopropyl | H | COC$_{11}$—H$_{23}$-n |
| Cyclopropyl | COCH$_3$ | COC$_2$H$_5$ |
| Cyclopropyl | COC$_3$H$_7$-n | COC$_6$H$_{13}$-n |
| Cyclopropyl | COCH$_3$ | COC$_3$H$_7$-n |
| Cyclopropyl | COC$_2$H$_5$ | COC$_3$H$_7$-n |
| Cyclopropyl | H | COCyclopropyl |
| Cyclopropyl | COCyclopropyl | COCyclopropyl |
| Cyclopropyl | COCH$_3$ | COCH$_3$ |
| Isopropyl | H | H |
| Isopropyl | H | COCH$_3$ |
| Isopropyl | H | COC$_3$H$_7$-n |
| Cyclopropyl | H | CONHCH$_3$ |
| Cyclopropyl | H | CONHC$_3$H$_7$-i |
| Cyclopropyl | CONHCH$_3$ | CONHCH$_3$ |
| Cyclopropyl | H | SCNHCH$_3$ |
| Cyclopropyl | H | CONHCH$_2$CH=CH$_2$ |
| Cyclopropyl | CONHCH$_2$CH=CH$_2$ | CONHCH$_2$CH=CH$_2$ |
| Cyclopropyl | CSNHCH$_3$ | CSNHCH$_3$ |

The active compounds having the common names propoxur, cyfluthrin, flumethrin, pyriproxyfen, methoprene, diazinon, amitraz and levamisol may be singled out in particular.

The shaped articles can furthermore comprise the additives customary for plastics. Customary additives are, for example, pigments, stabilizers, flow agents, glidants and mould release agents.

In the examples which follow, 1-[(6chloro-3-pyridinyl)methyl]-N-nitro-2-imidazolidinium (common name imidacloprid) is employed as active compound.

EXAMPLE 1

SC (Suspension concentrate) formulation:

368 g of imidacloprid
35 g of block copolymer of emulsifier ethylene oxide and propylene oxide
12 g of ditolyl ether sulphonate/formaldehyde condensate (emulsifier)
3.5 g of water-soluble polyvinyl alcohol
58.0 g of NH$_4$Cl
116.0 g of urea
1.2 g of (37% strength aqueous hydrochloric acid)
4.6 g of xanthan gum
560.5 g of distilled water

EXAMPLE 2

WP (dispersible powder) formulation
25.0 g of imidacloprid
1.0 g of diisobutyl-naphthalene-Na-sulphonate
10.0 g of n-dodecylbenzylsulphonic acid calcium
12.0 g of highly disperse silica-containing alkylaryl polyglycol ether
3.0 g of ditolyl ether sulphonate/formaldehyde condensate (emulsifier)
2.0 g of ®Baysilon-E, a silicone-containing antifoam by Bayer AG
2.0 g of finely disperse silicon dioxide and
45.0 g of kaolin

EXAMPLE 3

SL (water-soluble concentrate) formulation
18.3 g of imidacloprid
2.5 g of neutral emulsifier based on alkylaryl polyglycol ethers
3.5 g of sodium diisocel sulphosuccinate
38.4 g of dimethyl sulphoxide and
37.5 g of 2-propanol

EXAMPLE 4

SL (water-soluble concentrate) formulation
185 g of imidacloprid
5.0 g of sodium diisooctyl sulphosuccinate and
76.5 g of dimethyl sulphoxide
are added to a 100 g shampoo formulation composed of
44.4% by weight of Marlon AT 50, a triethanolamine salt of alkylbenzenesulphonic acids by Hüls AG
11.1% by weight of Marlon AT 350, sodium salt of alkylbenzenesulphonic acids by Hüls AG
3.0% by weight of condensation product of oleic acids and diethanolamine by Hüls AG and
41.5% by weight of polyethylene glycol.

EXAMPLE 5

Spray formulation composed of
2.0 g of imidacloprid
10.0 g of dimethyl sulphoxide
35.0 g of 2-propanol and
53.0 g of acetone

EXAMPLE 6

Pour-on formulation
20.3 g of imidacloprid
1.8 g of polyvinyl alcohol
1.8 g of block copolymer based on ethylene oxide and propylene oxide
0.26 g of xanthan gum
9.0 g of glycerol
59.2 g of distilled water

EXAMPLE 7

Composition:
imidacloprid 10.00 g
di-n-butyl adipate 21.10 g
diethylhexyl phthalate 9.10 g
epoxidised soybean oil 2.30 g
stearic acid 0.80 g
PVC 56.70 g
Preparation:

A mixture of di-n-butyl adipate, diethylhexyl phthalate and epoxidised soybean oil is added to a homogeneous mixture of imidacloprid and PVC in a mixer. Mixing is continued until the mixture is homogeneous. If the mixture is heated during the mixing process, e.g. by increasing the number of revolutions of the mixer, the plasticiser mixture is more readily incorporated into the PVC. After the subsequent homogeneous distribution of the stearic acid the mixture is injection-moulded to form dog collars.

EXAMPLE 8

Composition:
imidacloprid 10.00 g
epoxidised soybean oil 2.30 g
stearic acid 0.80 g
acetyltributyl citrate 30.20 g
PVC 56.70 g
Preparation:

The mixture of acetyltributyl citrate and epoxidised soybean oil is applied to a homogeneous mixture of imidacloprid and PVC in a mixer. If the mixture is heating during the mixing process the plasticiser mixture is more readily incorporated into the PVC; mixing is continued until the mixture is homogeneous. The mixture is extruded to form dog collars by a conventional method.

EXAMPLE 9

Composition:
imidacloprid 20.00 g
epoxidised soybean oil 2.30 g
stearic acid 0.80 g
acetyltributyl citrate 30.20 g
PVC 46.70 g
Preparation:
as in Example 8

EXAMPLE 10

Composition:
imidacloprid 7.50 g
epoxidised soybean oil 10.00 g
stearic acid 0.80 g
acetyltributyl citrate 15.00 g
PVC 66.70 g
Preparation:
as in Example 8

EXAMPLE 11

Composition:
imidacloprid 10.00 g
epoxidised soybean oil 2.30 g
stearic acid 0.80 g
triacetin 15.00 g
PVC 71.90g
Preparation:

The mixture of triacetin and soybean oil is applied to the homogeneous mixture of PVC and imidacloprid in a mixer. If the mixture is heated, for example by increasing the number of revolutions of the mixer, the plasticiser is more readily incorporated into the PVC. After adding stearic acid homogeneously, the mixture is extruded into sheets in an extruder, from which medallions (=attachments for collars) are punched.

EXAMPLE 12

Composition:
imidacloprid 5.00 g
polyether block amide (Pebax®) 94.50 g
Preparation:
The active compound is applied to the substrate in a high-power mixer and the mixture is injection-moulded to form dog collars.

EXAMPLE 13

Composition:
imidacloprid 10.00 g
medium-chain triglycerides 15.00 g
highly dispersed silicon dioxide 0.50 g
polyether block amide (Pebax®) 74.50 g
Preparation:
Medium-chain triglycerides are applied to the homogeneous mixture of imidacloprid and the polyether block amide in a mixer. If the mixture is heated the medium-chain triglycerides are more readily incorporated into the polyether block amide. To improve flowability highly dispersed silicon dioxide is added homogeneously before extruding the mixture. Sheets are extruded from which medallions (=attachments for collars) are punched.

EXAMPLE 14

Composition:
imidacloprid 10.00 g
styrene-butylene block
copolymer (Thermolast® K) 90.00 g
Preparation:
The active compound is applied to the substrate in a high-power mixer and the mixture is injection-moulded to form collars.

EXAMPLE 15

Composition:
imidacloprid 5.00 g
copolyester (Hytrel®) 95.00 g
Preparation:
The mixture is extruded to form dog collars by a conventional method.

EXAMPLE 16

Composition:
imidacloprid 10.00 g
polyether block amide (Pebax®) 90.00 g
Preparation:
The homogeneous mixture is extruded into sheets in an extruder, from which medallions (=attachments for collars) are punched.

EXAMPLE 17

Composition:
imidacloprid 10.00 g
medium-chain triglycerides 30.00 g
highly dispersed silicon dioxide 0.50 g
polyether block amide (Pebax®) 59.50 g
Preparation:
as in Example 13

EXAMPLE A 1 ml of the SC formulation described in Example 1 was applied in the form of a pour-on solution to the shoulder of a dog infested with 200 fleas. The test animal was immediately freed from adult fleas. The treatment according to the invention results in a 100% mortality rate of the fleas.

USE EXAMPLE A 1 ml of the formulation described in Example 1 was diluted in 1 l of water, and this solution was poured over dogs which were infested with fleas until the dogs were dripping wet. The following results were obtained:

| Period | Number of fleas per dog | | % Action |
|---|---|---|---|
| Day | untreated | treated | |
| −1 Infestation with 100 fleas | 30 | 0 | 100 |
| 0 Treatment and counting | | | |
| 5, 8 Infestation with 100 fleas | 56 | 0 | 100 |
| 9 Counting | | | |
| 15 Infestation with 100 fleas | 76 | 0 | 100 |
| 16 Counting | | | |
| 19 Infestation with 100 fleas (untreated animals) 250 fleas (treated animals) | 39 | 0 | 100 |
| 20 Counting | | | |
| 26 Infestation with 100 fleas | 43 | 0 | 100 |
| 27 Counting | | | |

USE EXAMPLE B 1 ml of the solution in accordance with Example 1 were applied to a dog's shoulder. 2 and 6 days after the treatment, the animal was infested with 200 fleas. In each case on day 3 and day 7 after the treatment, the fleas remaining on the dogs were counted. No live fleas were found. A 100% action was obtained.

What is claimed is:
1. A method for non-systemically controlling a parasitic insect selected from fleas and lice on a human or animal, said method comprising contacting said parasitic insect with an effective amount therefor of a compound of the formula:

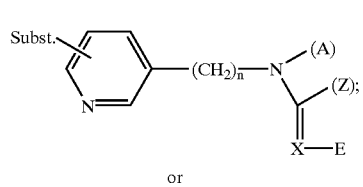

(II)

or

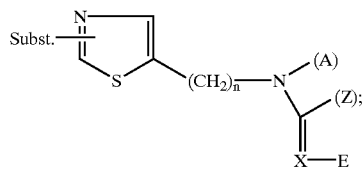

(III)

wherein n represents 1 or 2;

Subst. represents halogen;

A and Z together with the nitrogen and cabon atom to which they are bonded form a saturated heterocyclic ring having 6 ring members, said heterocyclic ring optionally containing in addition to the nitrogen atom to which A is bonded a further hetero atom, said hetero atom being selected from the group consisting of oxygen and sulfur;

E represents $NO_2$ or CN; and

X represents —CH= or —N=;

wherein said contacting of said parasitic insect with said compound is effected by:

a) topically applying said compound to the dermis of said human or animal; or b) contacting the dermis of said human or animal with an article containing said compound.

2. The method according to claim 1, wherein the animal is a dog or cat infested wih fleas.

3. The method according to claim 2, wherein said contacting is effected by applying said compound topically to the dermis of said dog or cat by a pou-on or spot-on method.

4. The method according to claim 2, wherein said contacting is effected by contacting the dermis of said dog or cat with an article containing said compound.

5. The method according to claim 1, wherein is carried out on a human, and the human is infected with lice.

* * * * *

UNITED STATES PATENT AND TRADEMARK OFFICE
CERTIFICATE OF CORRECTION

PATENT NO. : 6,429,206 B2
DATED : August 6, 2002
INVENTOR(S) : Hubert Dorn and Terence Hopkins It is certified that error appears in the above-identified patent and that said Letters Patent is hereby corrected as shown below:

Column 28,
Line 18, change "wherein" to -- which --

Signed and Sealed this

Eleventh Day of February, 2003

JAMES E. ROGAN
*Director of the United States Patent and Trademark Office*